(12) United States Patent
Emmett et al.

(10) Patent No.: US 7,601,542 B2
(45) Date of Patent: Oct. 13, 2009

(54) ANALYTICAL METHOD FOR PROTEIN MAPPING USING HYDROGEN/DEUTERIUM EXCHANGE

(75) Inventors: Mark R. Emmett, Monticello, FL (US); Sasa Kazazic, Tallahassee, FL (US); Alan G. Marshall, Tallahassee, FL (US); Michael J. Greig, Carlsbad, CA (US)

(73) Assignee: Florida State University Research Foundation, Tallahassee, FL (US)

(*) Notice: Subject to any disclaimer, the term of this patent is extended or adjusted under 35 U.S.C. 154(b) by 234 days.

(21) Appl. No.: 11/672,789

(22) Filed: Feb. 8, 2007

(65) Prior Publication Data

US 2007/0224642 A1 Sep. 27, 2007

Related U.S. Application Data

(60) Provisional application No. 60/771,542, filed on Feb. 8, 2006.

(51) Int. Cl.
*G01N 33/00* (2006.01)
(52) U.S. Cl. .......................... 436/86; 436/161; 435/7.1; 435/23; 210/634; 210/136; 210/656; 73/61.56; 422/69; 422/103
(58) Field of Classification Search ........................ None
See application file for complete search history.

(56) References Cited

OTHER PUBLICATIONS

Bolanos, Ben, et al., SFC/MS in drug discovery at Pfizer, La Jolla, 2004, International Journal of Mass Spectroetry, vol. 238, pp. 85-97.*
Wang, et al., "Conformational and Dynamic Chanages of Yersinia Protein Tyrosine Phosphatase Induced by Ligand Binding and Active Site Mutation and Revealed by H/D Exchange and Electrospray Ionization Fourier Transform Ion Cyclotron Resonance Mass Spectrometry," Biochemistry, 37:15289-99 (1998).
Emmett, et al., "Supercritical Fluid Chromatography Reduction of Hydrogen/Deuterium Back Exchange in Solution-Phase Hydrogen/Deuterium Exchange with mass Spectrometric Anaylysis," Anal. Chem. 78:7058-60 (2006).
Wikipedia, Title: "High Performance Liquid Chromatography," Feb. 8, 2006, pp. 1-3.

* cited by examiner

*Primary Examiner*—Yelena G Gakh
*Assistant Examiner*—Robert Xu
(74) *Attorney, Agent, or Firm*—Sutherland Asbill & Brennan LLP

(57) ABSTRACT

Analytical methods using hydrogen/deuterium exchange are provided which reduce or eliminate the back-exchange of deuterium for hydrogen. The methods, which are useful in protein and peptide mapping, include the steps of (a) providing a peptide or protein comprising a solvent accessible hydrogen; (b) exchanging the solvent accessible hydrogen for a deuterium; (c) separating the peptide or protein with supercritical fluid chromatography; and (d) analyzing by mass spectrometry the mass of the separated peptide or protein. Supercritical fluid chromatography enables the observation of fast exchanging hydrogen atoms missed using conventional liquid chromatography methods.

15 Claims, 3 Drawing Sheets

ANALYTICAL METHOD FOR PROTEIN MAPPING USING HYDROGEN/DEUTERIUM EXCHANGE

CROSS-REFERENCE TO RELATED APPLICATIONS

This application claims benefit of U.S. Provisional Application No. 60/771,542, filed Feb. 8, 2006. The application is incorporated herein by reference.

STATEMENT REGARDING FEDERALLY SPONSORED RESEARCH OR DEVELOPMENT

This invention was made with U.S. government support under Contract No. CHE-99-09502 awarded by the National Science Foundation. The U.S. government has certain rights in the invention.

BACKGROUND OF THE INVENTION

This invention is generally in the field of protein or peptide mapping, and more particularly relates to mapping that utilizes hydrogen/deuterium exchange.

Proteins contain covalently bonded hydrogen atoms that are known to exchange with hydrogen atoms found in a surrounding solvent. Thus, if the solvent surrounding a protein is changed from normal water ($H_2O$) to heavy water ($D_2O$), the exchange of hydrogen ($^1H$) for deuterium ($^2H$) can be observed. This exchange reaction, known as hydrogen-deuterium exchange (HDX), increases the molecular mass of the protein because the deuterium nucleus is heavier than the common proton. Since the hydrogen-deuterium exchange rate reflects the exposure level of the particular hydrogen atom to the solvent, spectrometric analysis can be utilized subsequent to HDX to determine which portions of the protein have increased in molecular mass and thus are accessible to the surrounding solvent. This information can be extremely useful in understanding protein conformation, protein/protein interactions, and protein/ligand interactions See Wang, et al., *Biochemistry* 37:15289-99 (1998). For example, this "mapping" information may be used to determine protein-ligand binding sites and is used in the pharmaceutical industry for intelligent drug design.

Determining which portions of a protein have increased in molecular mass due to HDX (and thus which portions of a protein are in contact with the surrounding solvent) generally requires a protein digestion step, a desalting/separation step, and a spectrometric analysis step. Currently, the separation technology used in HDX experiments is reversed phase high performance liquid chromatography (RP-HPLC). Unfortunately, the mobile phase used in RP-HPLC is predominately water. The presence of water is a major drawback because it allows for the back-exchange of deuterium for hydrogen during the separation step immediately prior to the spectrometric analysis. Back-exchange is a major problem with solution HDX, as the back-exchange undesirably reduces both the amount and the resolution of the resulting data. It would therefore be useful to provide a method that eliminates, or at least substantially reduces, back-exchange during separation.

In order to limit back-exchange, RP-HPLC conventionally is performed at 0-4° C. and under very fast gradients in order to limit the period in which the sample is in contact with the aqueous phase. Unfortunately, this separation method reduces the reversed-phase chromatographic resolution, and increases the complexity of the spectra. Although reduced chromatographic resolution can be partially offset through the use of high resolution Fourier transform ion cyclotron resonance mass spectrometry (FT-ICR MS), these techniques still allow for the back exchange of deuterium for hydrogen. It therefore would be desirable to eliminate, or at least substantially reduce, back-exchange during separation while maintaining a high degree of chromatographic resolution.

BRIEF SUMMARY OF THE INVENTION

Analytical methods and apparatus which use hydrogen/deuterium exchange are provided. In one aspect an analytical method is provided that includes the steps of: (a) providing a protein or peptide, which protein or peptide comprises at least one solvent accessible hydrogen; (b) exchanging the at least one solvent accessible hydrogen for at least one deuterium to make a deuterated protein or peptide; (c) using supercritical fluid chromatography to separate the deuterated protein or peptide; and (d) analyzing the mass of the separated protein or peptide. The analysis of step (d) preferably includes mass spectrometry. The method may further include the step of digesting the peptide or protein after step (b) and before step (c).

The step of exchanging the at least one solvent accessible hydrogen for the at least one deuterium may comprise exposing the peptide or protein to a deuterated buffer. In one particular embodiment, the step of using supercritical fluid chromatography to separate the deuterated peptide or protein is conducted at about 1° C.

The supercritical fluid chromatography preferably utilizes a mobile phase that comprises a supercritical fluid, such as carbon dioxide. In another embodiment, the supercritical fluid chromatography utilizes a mobile phase that comprises a gas at a non-supercritical state of enhanced fluidity. The supercritical fluid chromatography may utilize a mobile phase modifier that comprises a polar or non-polar solvent. Examples of possible solvents include acetonitrile, dimethyl sulfoxide, dimethyl formamide, tetrahydroforan, dimethyl acetamide, trichloroethane, acetone, ethanol, methanol, isopropanol, ethyl acetate, formic acid, water, and mixtures thereof.

In one particular embodiment, an analytical method using hydrogen/deuterium exchange is provided that includes the steps of: (a) obtaining a protein or peptide, which protein or peptide comprises at least one solvent accessible hydrogen; (b) exposing the peptide or protein to a deuterated buffer solution to effect exchanging the at least one solvent accessible hydrogen for at least one deuterium, thereby making a deuterated protein or peptide; (c) mixing the deuterated protein or peptide with a peptidase to produce a digested deuterated protein or peptide; (d) using supercritical fluid chromatography to separate the digested deuterated protein or peptide; and (e) using mass spectrometry to analyze the mass of the separated protein or peptide obtained from step (d).

In another aspect, an apparatus is provided for protein or peptide analysis, which apparatus includes a supercritical fluid chromatograph; and a mass spectrometer, wherein the hydrogen-deuterium exchange is coupled to the mass spectrometer so that the supercritical fluid chromatograph can separate and desalt a protein or peptide sample prior to mass analysis of the protein or peptide sample by the mass spectrometer. The apparatus may further include robotic means for carrying out hydrogen-deuterium exchange on the protein or peptide sample and for feeding the deuterated sample to the supercritical fluid chromatograph. The mass spectrometer may be equipped with an electrospray ionization source. The apparatus may further include means for cooling the protein or peptide sample.

In another aspect, a method of protein or peptide mapping is provided that includes the steps of: (a) selecting a non-deuterated protein or complex to be mapped, which protein or complex comprises at least one solvent accessible hydrogen; (b) exchanging the at least one solvent accessible hydrogen for at least one deuterium to make a deuterated protein or peptide; (c) using supercritical fluid chromatography to separate the deuterated protein or peptide; (d) analyzing the mass of the separated protein or peptide; and (e) comparing mass information from the non-deuterated protein or complex with mass information from the separated protein or peptide to yield information about the structure of the protein or complex.

DETAILED DESCRIPTION OF THE INVENTION

Figure 1:
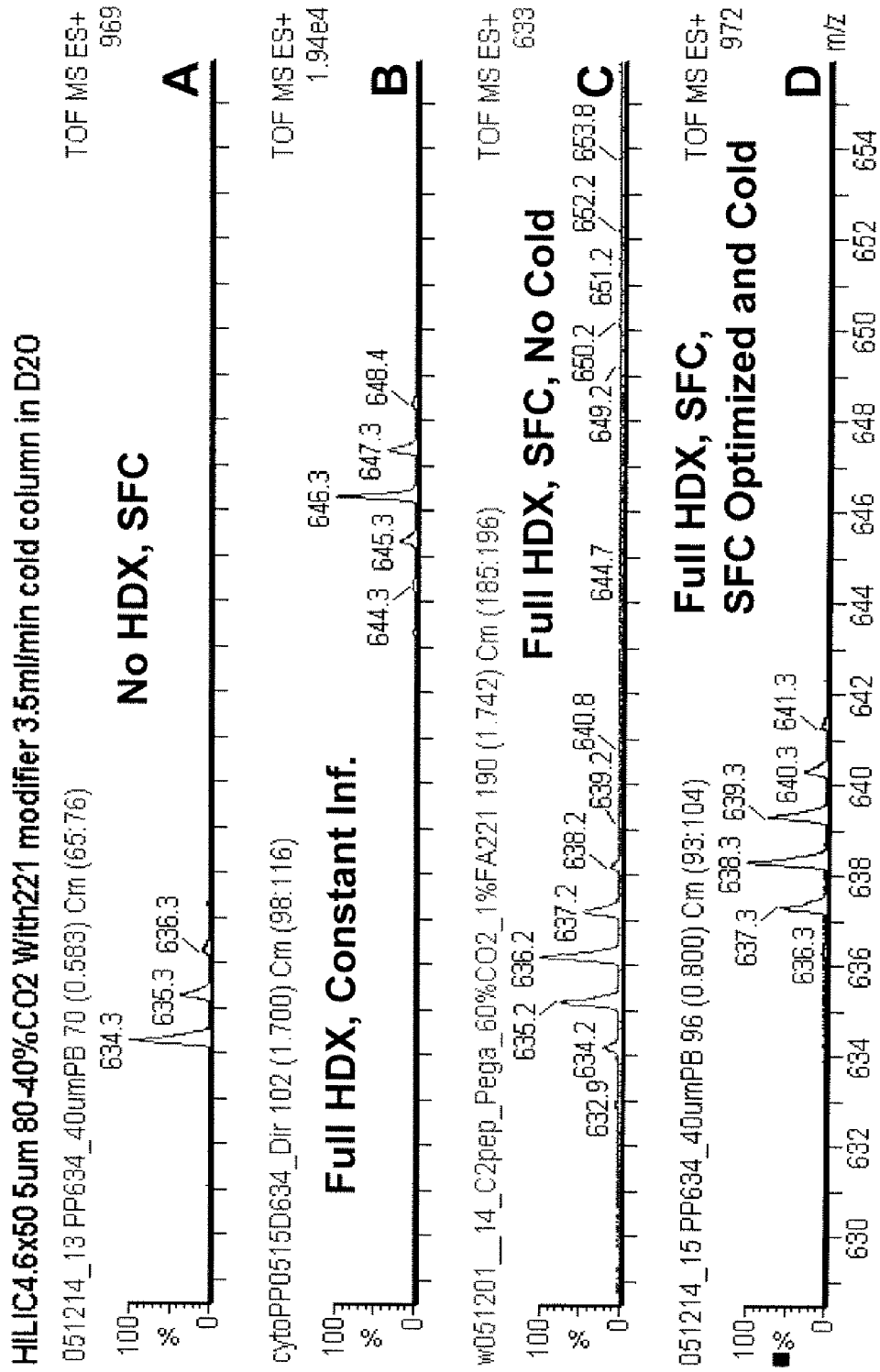
FIG. 1A is a mass spectrum of a non-deuterated peptide following supercritical fluid chromatography at room temperature.
FIG. 1B is a mass spectrum of a deuterated peptide without any chromatography.
FIG. 1C is a mass spectrum of a deuterated peptide following supercritical fluid chromatography at room temperature.
FIG. 1D is a mass spectrum of a deuterated peptide following supercritical fluid chromatography at 1° C.

Improved methods and apparatus have been developed for protein or peptide mapping by hydrogen/deuterium exchange. Studies have shown that conventional HDX methods lose up to 90% of the data at the earliest stages of H/D exchange. It has now been discovered that by using supercritical fluid chromatography (SFC) as the peptide separation/desalting technique following hydrogen/deuterium exchange, one advantageously can reduce the back exchange of deuterium for hydrogen to near immeasurable levels. See Emmett, et al. *Anal. Chem.* 78:7058-60 (2006).

This reduction of back exchange can improve the spatial resolution of the protein-solvent interface by increasing the amount of data that is obtained by the spectrometric analysis. The mobile phase in SFC is predominately a gas that is in a supercritical or enhanced fluidity state. Preferably, the mobile phase has no exchangeable hydrogens and thus essentially eliminates the back-exchange observed in conventional RP-HPLC separations. It also has been beneficially discovered that these methods and apparatus allow access to crucial structural information that has been lost in HDX experiments that use conventional separation methods. By using supercritical fluid chromatography instead of high performance liquid chromatography, the faster exchanging hydrogen atoms that have been missed in previous HDX experiments are now observable.

The Methods

Protein or peptide mapping or other analysis is performed using HDX, while eliminating or reducing the back-exchange of deuterium for hydrogen. In a preferred embodiment, the analytical methods include the steps of (a) providing a protein or peptide, which protein or peptide comprises at least one solvent accessible hydrogen; (b) exchanging the at least one solvent accessible hydrogen for at least one deuterium to make a deuterated protein or peptide; (c) using supercritical fluid chromatography to separate the deuterated protein or peptide; and (d) analyzing the mass of the separated protein or peptide.

The methods described herein are useful in mapping essentially any protein or peptide. As used herein, the term "peptide" generally refers to a linear chain of around 2 to 40 amino acids joined together with peptide bonds, and the term "protein" generally refers a linear chain of around 30 or more amino acids joined together with peptide bonds. The term "solvent accessible hydrogen" refers to a hydrogen atom located in a position in the protein or peptide such that in solution, the hydrogen atom is exposed to the solvent surrounding the protein or peptide. The amide hydrogen (hydrogen bonded to the amide nitrogen) is the exchangeable hydrogen that is most commonly monitored in HDX experiments.

The step of exchanging the solvent accessible hydrogen for a deuterium can be done using essentially any process that effects the exchange of accessible hydrogen atoms for deuterium atoms. In one embodiment, the solvent accessible hydrogen may be exchanged for a deuterium by exposing a solution of a peptide or protein by dilution of the protein sample into a deuterated buffer. Typically a 1/10 or 1/20 dilution is made, although dilution ratios may be varied. The "deuterated buffer" is essentially any solution in which the ratio of deuterium ($^2$H) to hydrogen ($^1$H) is greater than the ratio of deuterium to hydrogen in the protein or peptide. In a preferred embodiment, the protein/protein complex is digested by a peptidase to produce smaller peptide fragments. Suitable peptidases are known in the art.

The step of separating the deuterated peptides or proteins using supercritical chromatography generally involves a separation or purification technique that includes feeding the deuterated peptides or proteins into/through the stationary phase using a supercritical fluid as the mobile phase, to yield separated proteins and peptides. As used herein, the phrase "separating the peptide or protein" refers to the complete or partial isolation of least one peptide or protein from at least one other salt, solvent, peptide, or protein, and the term "separated peptide or protein" refers to at least one peptide or protein that has been completely or partially isolated from at least one other salt, solvent, peptide, or protein.

As used herein, the term "supercritical fluid" refers to essentially any suitable mobile phase at a temperature and pressure above its thermodynamic critical point. In another embodiment, the mobile phase may consist of a gas at a non-supercritical state of enhanced fluidity. In various embodiments, the mobile phase may comprise carbon dioxide, nitrous oxide, or other gas that does not have an exchangeable hydrogen. The mobile phase may further include a mobile phase modifier, such as a polar or non-polar solvent. Non-exchangeable solvents are preferred. Examples of solvents that may be useful in the methods described herein include acetonitrile, dimethyl sulfoxide, dimethyl formamide, tetrahydroforan, dimethyl acetamide, trichloroethane, acetone, ethanol, methanol, isopropanol, ethyl acetate, formic acid, water, and mixtures thereof. In one embodiment, the deuterated protein or peptide undergoes a digestion step before the step of separating the peptides or proteins with supercritical fluid chromatography. Analysis of smaller peptide fragments enhances the resolution of the location in the protein in which the deuterium has been incorporated, thus permitting a better assessment of the solvent accessibility of the intact protein/protein complex.

The step of analyzing the mass of the separated peptide or protein may comprise essentially any suitable technique known in the art. In a preferred embodiment, the step includes using mass spectrometry to determine the masses of the separated deuterated proteins and peptides. Analytical techniques and equipment for this are well known in the art. High resolution mass spectrometry instrumentation (FT-ICR MS) is preferred, but other lower resolution instruments such as quadrupole, TOF, ion traps or orbitraps may also be used in the analysis. The method of sample ionization may also vary, in this embodiment electrospray ionization was used.

The information obtained from analyzing the mass of the peptide or protein can be extremely useful in understanding protein confirmation, protein/protein interactions, and protein/ligand interactions. For example, HDX coupled to SFC can be used to characterize protein interactions with other molecules. By performing hydrogen-deuterium exchange on both the isolated protein and the protein bound to another molecule, the region of the protein that is protected from the solvent by the other molecule can be observed. This data can be used to build a model of how the protein interacts with the molecule, which can be extremely valuable for intelligent drug design. By using supercritical fluid chromatography to eliminate or reduce the back-exchange of deuterium for hydrogen, the fastest exchanging hydrogen atoms that have been missed in previous HDX experiments can be observed to provide a better understanding of which protein regions interact with the other molecule. Furthermore, HDX coupled to SFC can be used to characterize the folding pathway of proteins. By refolding a protein while performing hydrogen-deuterium exchange, the parts of the protein that fold first will be protected from the deuterated solvent more quickly than the areas of the protein that fold later. By using supercritical fluid chromatography to eliminate or reduce the back-exchange of deuterium for hydrogen, the resolution of this information can be increased to provide a better understanding about how the protein folds.

The Apparatus

Figure 3:
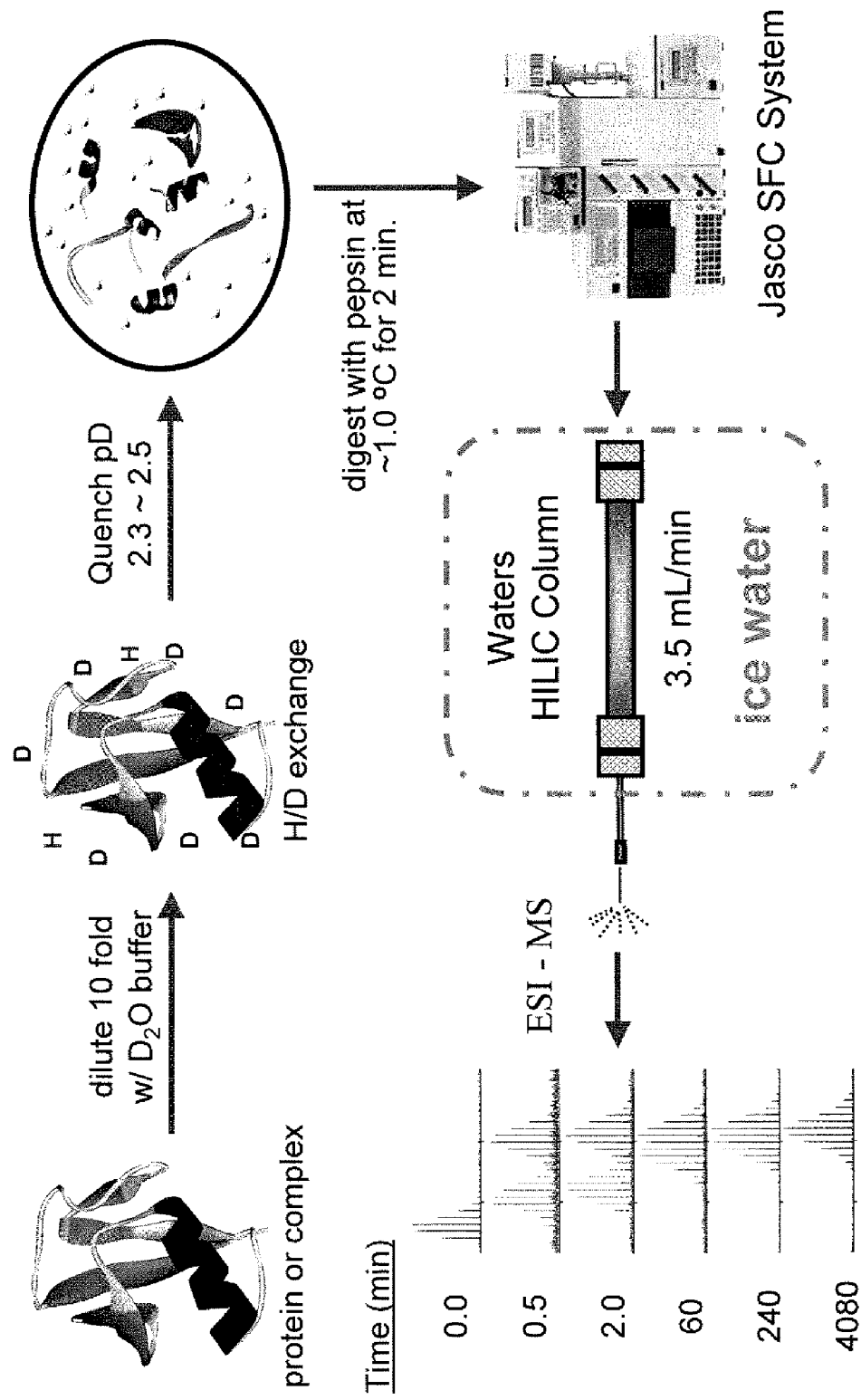
FIG. 3 is an illustration and process flow diagram of one embodiment of the method and apparatus for carrying out the analytical processes described herein.

One skilled in the art can readily adapt and connect conventional chromatography equipment and materials together with a mass spectrometer, suitably configured to practice the methods described herein. The ionization source should be configured to eliminate the freezing of the SFC eluent as it changes from a supercritical fluid/enhanced fluid to a gas. In one embodiment, the SFC eluent is post-column split to reduce the flow rate to the ion source of the mass spectrometer and the ion source is heated to eliminate freezing of the SFC mobile phase. The apparatus comprises a supercritical fluid chromatograph operably coupled to a mass spectrometer. One embodiment is illustrated in FIG. 3.

The supercritical fluid chromatography system includes a back pressure regulating device to maintain the system pressure above the critical pressure (Pc) of the fluid used, from a delivery pump through to the detector. The back pressure device may be a simple restrictor (e.g., an orifice) or a mechanical or electronic feedback regulator. The system may include a thermostat and heat exchanger means (e.g., a chiller) to aid in start-up and/or in helping to keep the temperature of the mobile phase fluid above its critical temperature (Tc).

When the mobile phase includes a solvent with an exchangeable hydrogen, then the apparatus preferably includes a cooling component for keeping the deuterated protein or peptide sample chilled throughout the steps of sample quenching, dilution, digestion, SFC injection, separation, and to the mass spectrometry analysis, so that back exchange is minimized.

In one embodiment, the apparatus includes Fourier-transform ion cyclotron resonance mass spectrometry (FT-ICR). The apparatus can be made completely automated. In one embodiment, the apparatus can be a specific solution HDX system utilizing robotics coupled to SFC with mass spectrometric analysis.

The methods and apparatus described above will be further understood with reference to the following non-limiting examples.

EXAMPLES

The following materials and equipment were used in the examples: HDX and sample injections were performed with a LEAP robot (Carboro, N.C.) programmed with interlaced software developed at the National High Magnetic Field Laboratory (NHMFL). SFC was performed with a Jasco system (Easton, Md.) consisting of a PU-1580 $CO_2$ delivery pump, a PU-1580 Intelligent HPLC pump (for modifier delivery) and a BD-158-81 back pressure regulators. SFC effluent was monitored by a Waters Micromass (Milford, Mass.) LCT ESI-TOF mass spectrometer equipped with a Z-spray ESI source. Each HDX sample (10 µL at 40 M) was separated on a 4.6 mm×50 mm Waters Atlantis HILIC 5 micron silica column. Gradient elution was performed from 80% $CO_2$ to 40% $CO_2$ in 4 minutes at 3.5 mL/min. The mobile phase modifier was 40% acetonitrile, 40% methanol, 19% $H_2O$, and 1% formic acid.

Example 1

HDX-SFC of a Small Peptide

The smallest peptic fragment normally produced by the digestion of a protein is 5 amino acids in length. Thus, a synthetic penta-peptide IFVQK was utilized to test for the retention of a small peptic fragment on a SFC column. IFVQK has 4 exchangeable amide hydrogens, and a non-deuterated mass-to-charge ratio (m/z) of 634.3.

SFC-MS was first performed on the non-deuterated peptide at room temperature. As seen in FIG. 1A, running the non-deuterated peptide through the SFC column coupled to the mass spectrometer produced a spectrum with a peak appearing at 634.3 m/z, demonstrating that a small peptide can be retained on a SFC column.

Next, the fully deuterated peptide was electrosprayed directly from a deuterated solvent (i.e., with side chains also fully deuterated) into the mass spectrometer. As seen in FIG. 1B, the spectrum featured an average mass-to-charge ratio that was higher than 634.3 m/z due to the deuterium increasing the molecular weight of the peptide.

SFC-MS was then performed on the fully deuterated peptide at room temperature (22° C.). As seen in FIG. 1C, the spectrum of the eluted peptide had an isotopic distribution number-average m/z of about 636, indicating an average incorporation of two deuteriums.

Finally, SFC-MS was performed on the fully deuterated peptide at 1° C. and with a modified gradient (modifier held at 1° C. and supplemented with 1% formic acid). As seen in FIG. 1D, running the non-deuterated peptide through the SFC column under these conditions produced a spectrum with an isotopic distribution number-average m/z of about 638, indicating an average incorporation of the maximum possible four deuteriums from the exchangeable amide hydrogens. This result indicates near zero back-exchange of deuterium for hydrogen.

Example 2

HIDX-SFC of Myoglobin

Figure 2:
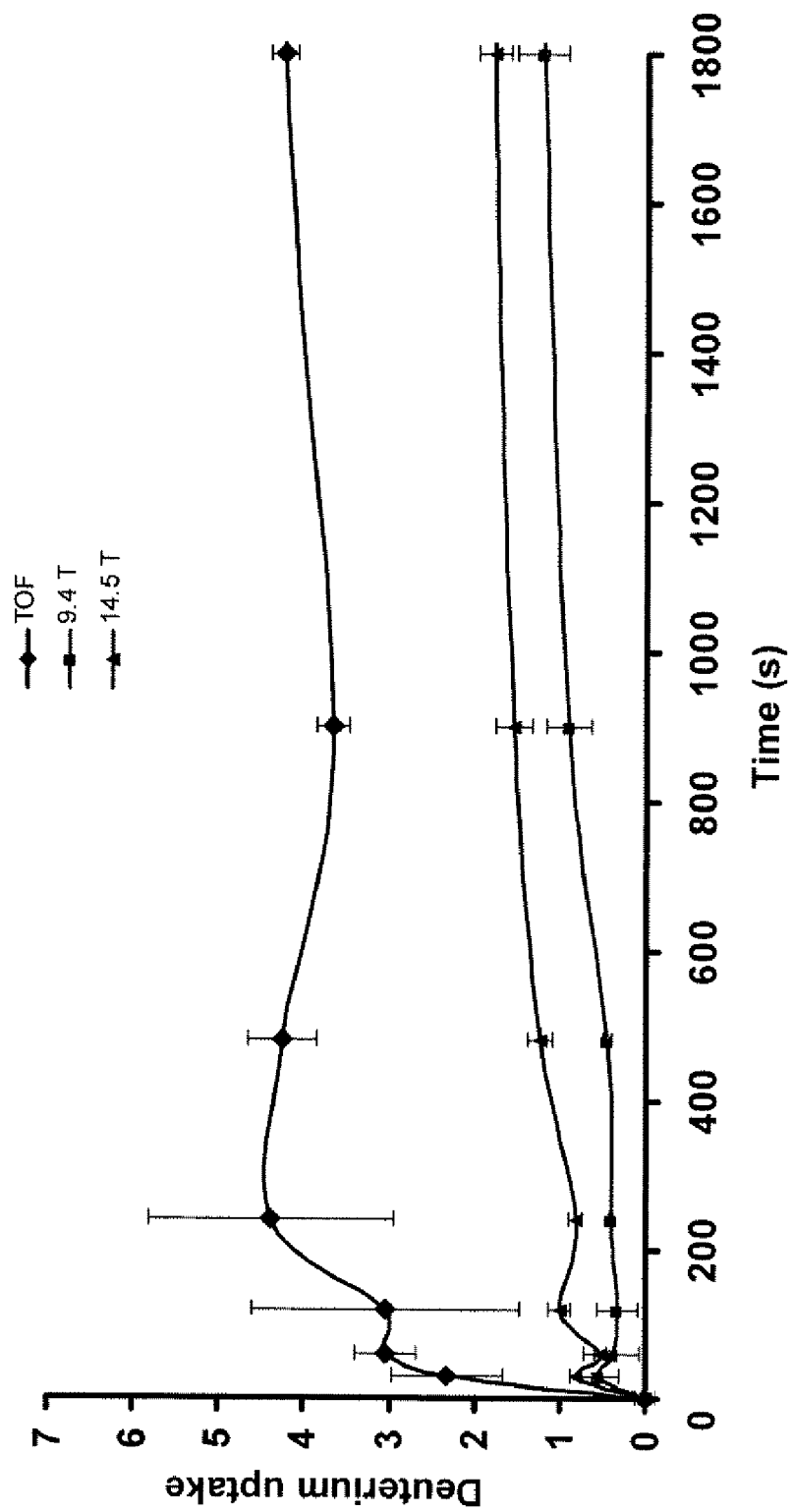
FIG. 2 is a graph comparing the level of deuterium uptake at various times for a myoglobin peptic fragment having undergone SFC-TOF, HPLC-FT-ICR at 9.4 T, and HPLC-FT-ICR at 14.5 T.

Deuterated myoglobin protein was digested into peptic fragments. (Myoglobin Peptic Fragment (aa. 56 to 69) KASELDLKKHGTVVL, m/z=[762.9376]$^{2+}$) Deuterium uptake was then calculated using three different techniques: (1) Supercritical fluid chromatography followed by time of flight mass spectrometry (SFC-TOF); (2) HPLC-FT-ICR at 9.4 T; and (3) HPLC-FT-ICR at 14.5 T. As seen in FIG. 2 and Table 1, deuterium incorporation was much higher in the SFC separated peptides than in the HPLC separated peptides at all time points in the experiment due to the reduced back exchange of deuterium for hydrogen. Furthermore, the SFC separated peptides had the most dramatic increase in deuterium incorporation during the earliest time points of the H/D exchange, which demonstrates how this method allows access to crucial information that has been lost in HDX experiments that use conventional separation methods. By using supercritical fluid chromatography instead of high performance liquid chromatography, the faster exchanging hydrogen atoms that appear during earlier time points are now observable.

TABLE 1

| | SFC-TOF | | | HPLC 9.4 T | | | HPLC 14.5 T | | |
|---|---|---|---|---|---|---|---|---|---|
| | Av. Mass | SD | D. uptake | Av. Mass | SD | D. uptake | Av. Mass | SD | D. Uptake |
| 0Ctrl | 1526.316 | 0.02 | 0.0 | 1526.012 | 0.12 | 0.0 | 1526.636 | 0.02 | 0.0 |
| 30 | 1528.632 | 0.66 | 2.3 | 1526.553 | 0.08 | 0.5 | 1527.437 | 0.22 | 0.8 |
| 60 | 1529.363 | 0.36 | 3.0 | 1526.403 | 0.08 | 0.4 | 1527.161 | 0.31 | 0.5 |
| 120 | 1529.363 | 1.57 | 3.0 | 1526.348 | 0.14 | 0.3 | 1527.638 | 0.24 | 1.0 |
| 240 | 1530.703 | 1.44 | 4.4 | 1526.420 | 0.08 | 0.4 | 1527.449 | 0.01 | 0.8 |
| 480 | 1530.562 | 0.41 | 4.2 | 1526.470 | 0.14 | 0.5 | 1527.866 | 0.05 | 1,2 |
| 900 | 1529.974 | 0.19 | 3.7 | 1526.914 | 0.22 | 0.9 | 1528.170 | 0.27 | 1.5 |
| 1800 | 1530.547 | 0.15 | 4.2 | 1527.227 | 0.18 | 1.2 | 1528.413 | 0.29 | 1.8 |
| 3600 | 1530.873 | 0.08 | 4.6 | 1527.528 | 0.14 | 1.5 | 1528.484 | 0.23 | 1.8 |

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An analytical method using hydrogen/deuterium exchange, comprising the steps of:
   (a) providing a protein or peptide, which protein or peptide comprises at least one solvent accessible hydrogen;
   (b) exchanging the at least one solvent accessible hydrogen for at least one deuterium to make a deuterated protein or peptide;
   (c) using supercritical fluid chromatography to separate the deuterated protein or peptide; and
   (d) analyzing the mass of the separated protein or peptide.

2. The method of claim 1, further comprising the step of digesting the peptide or protein after step (b) and before step (c).

3. The method of claim 1, wherein the step of exchanging the at least one solvent accessible hydrogen for the at least one deuterium comprises exposing the peptide or protein to a deuterated buffer.

4. The method of claim 1, wherein the step of using supercritical fluid chromatography to separate the deuterated peptide or protein is conducted at about 1° C.

5. The method of claim 1, wherein the supercritical fluid chromatography utilizes a mobile phase that comprises a supercritical fluid.

6. The method of claim 5, wherein the mobile phase comprises carbon dioxide.

7. The method of claim 1, wherein the supercritical fluid chromatography utilizes a mobile phase modifier that comprises a polar or non-polar solvent.

8. The method of claim 7, wherein the solvent is selected from the group consisting of comprises acetonitrile, dimethyl sulfoxide, dimethyl formamide, tetrahydroforan, dimethyl acetamide, trichloroethane, acetone, ethanol, methanol, isopropanol, ethyl acetate, formic acid, water, and mixtures thereof.

9. The method of claim 1, the supercritical fluid chromatography utilizes a mobile phase modifier that comprises a polar or non-polar solvent.

10. The method of claim 1, wherein the step of analyzing the mass of the separated peptide or protein comprises mass spectrometry.

11. An analytical method using hydrogen/deuterium exchange, comprising the steps of:
   (a) obtaining a protein or peptide, which protein or peptide comprises at least one solvent accessible hydrogen;
   (b) exposing the peptide or protein to a deuterated buffer solution to effect exchanging the at least one solvent accessible hydrogen for at least one deuterium, thereby making a deuterated protein or peptide;
   (c) mixing the deuterated protein or peptide with a peptidase to produce a digested deuterated protein or peptide;
   (d) using supercritical fluid chromatography to separate the digested deuterated protein or peptide; and
   (e) using mass spectrometry to analyze the mass of the separated protein or peptide obtained from step (d).

12. The method of claim 11, wherein the supercritical fluid chromatography utilizes (i) a mobile phase that comprises a supercritical fluid which consists essentially of carbon dioxide, and (ii) a mobile phase modifier which comprises a polar or non-polar solvent.

13. A method of protein or peptide mapping comprising using the results of the analytical method of claim 1 to determine structural properties of a peptide or protein.

14. A method of protein or peptide mapping comprising using the results of the analytical method of claim 11 to determine structural properties of a peptide or protein.

15. A method of protein or peptide mapping comprising:
(a) selecting a non-deuterated protein or complex to be mapped, which protein or complex comprises at least one solvent accessible hydrogen;
(b) exchanging the at least one solvent accessible hydrogen for at least one deuterium to make a deuterated protein or peptide;
(c) using supercritical fluid chromatography to separate the deuterated protein or peptide;
(d) analyzing the mass of the separated protein or peptide; and
(e) comparing mass information from the non-deuterated protein or complex with mass information from the separated protein or peptide to yield information about the structure of the protein or complex.

* * * * *